United States Patent [19]

Wang

[11] 3,992,149
[45] Nov. 16, 1976

[54] COLORIMETRIC METHOD FOR THE ANALYSIS OF RESIDUAL ANIONIC OR CATIONIC SURFACTANTS

[75] Inventor: Lawrence K. Wang, Troy, N.Y.

[73] Assignee: Calspan Corporation, Buffalo, N.Y.

[22] Filed: Feb. 18, 1975

[21] Appl. No.: 550,692

[52] U.S. Cl. .......................... 23/230 R; 23/230 M; 252/408
[51] Int. Cl.² ................ G01N 31/00; G01N 31/22; G01N 33/18; G01N 31/16
[58] Field of Search .................... 23/230 R, 230 M; 252/408

[56] References Cited
UNITED STATES PATENTS
3,725,006 4/1973 Brandstrom et al. ............. 23/230 R

OTHER PUBLICATIONS

Scott; George V., Spectrophotometric Determination of Cationic Surfactants with Orange II, Analytical Chemistry, Apr., 1968, pp. 768–773.

Swisher; R. D., Surfactant Biodegradation, Marcel Dekker Inc., New York, 1970, pp. 50–54.

*Primary Examiner*—Norman Yudkoff
*Assistant Examiner*—Dale Lovercheck
*Attorney, Agent, or Firm*—Allen J. Jaffe

[57] ABSTRACT

A method suitable for the rapid colorimetric testing of raw water supplies, domestic sewage or industrial wastes for determining the residual presence and concentration of either anionic or cationic surfactants. An appropriate dye will react with ionic surfactant and form a chloroform-soluble, colored complex in the presence of chloroform. The color intensity of the vigorously rocked and subsequently settled chloroform layer is proportional to the concentration of the "dye-ionic surfactant complex", and can then be measured by making spectrophotometric readings of the chloroform solution at the optimum wavelength of the instrument used.

8 Claims, 1 Drawing Figure

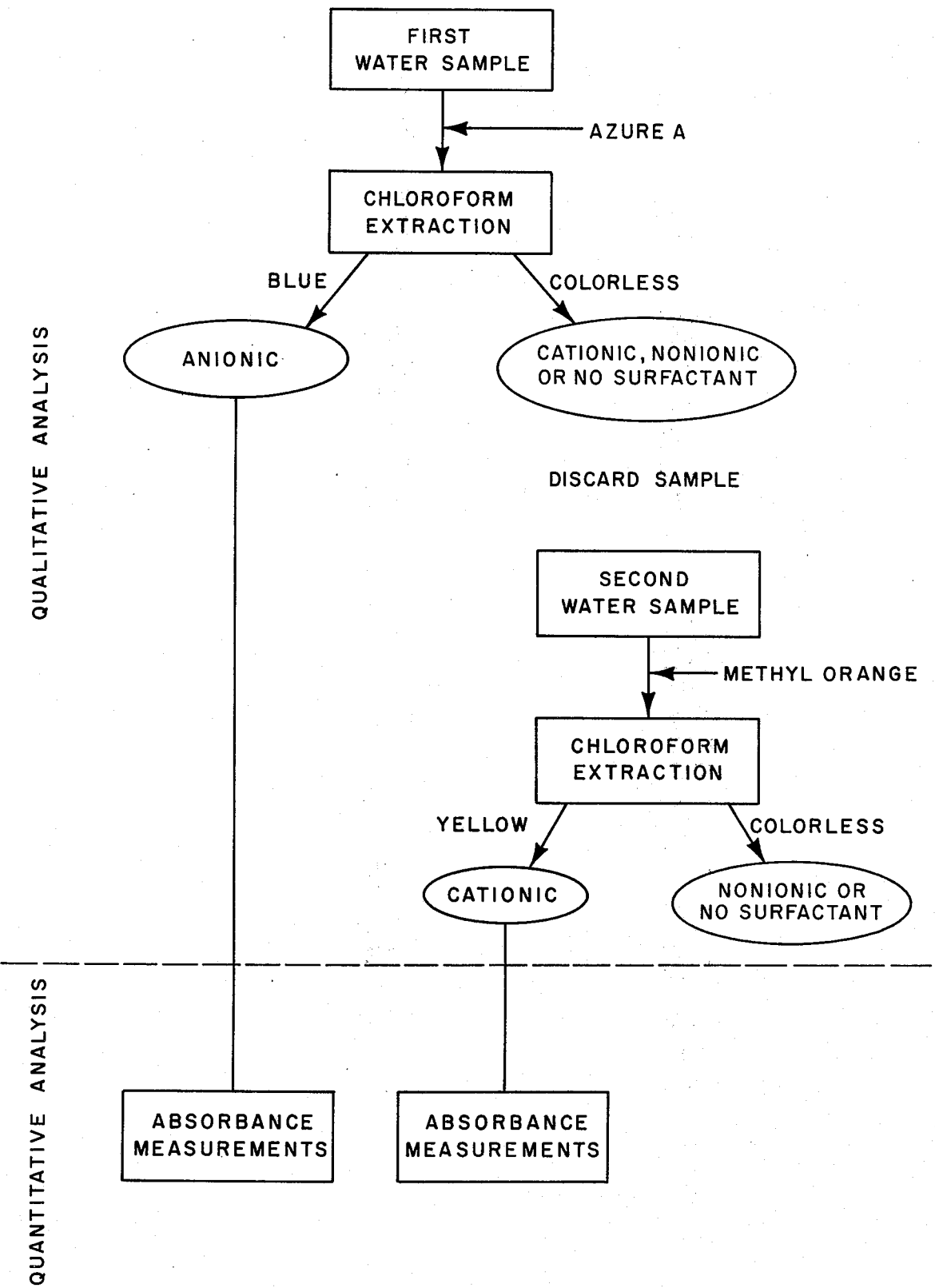

COLORIMETRIC METHOD FOR THE ANALYSIS OF RESIDUAL ANIONIC OR CATIONIC SURFACTANTS

The invention herein described was made in the course of or under a contract with the U.S. Army.

The present invention is a modified version of the method disclosed in my earlier filed application Ser. No. 385,775 filed Aug. 6, 1973, and permits field testing of water samples by personnel having limited training.

Residual anionic or cationic surfactants are often present in waste water effluents. Typical ionic surfactants present include linear alkylate sulfonate (LAS), an anionic surfactant widely used in synthetic detergents, and quaternary ammonium compounds, cationic surfactants widely used as sanitizers, flotation agents, primary coagulants, coagulant aids, softening agents, dyeing aids, corrosion inhibitors, algicides, and industrial detergents. Ordinarily, only one type of surfactant will be used since, to the degree that they are both present, anionic and cationic surfactants will interact to effectively remove each other as ionic surfactants. Thus, only one type of ionic surfactant will be present in a sample.

The wide usage of surfactants, particularly LAS which is toxic, necessitates the monitoring of water or waste water for the presence of ionic surfactants. The methylene blue method and the carbon adsorption method are the standard methods for the determination of anionic surfactants in aqueous solutions. Both of these methods are, however, time-consuming and suitable only for the analysis of anionic surfactants and, then, only under certain conditions. The titration method disclosed in my above-identified application can be used to determine either anionic or cationic surfactants accurately. However, the method of the present invention is more accurate at concentration ranges of 0.1 mg 1 to 3.0 mg 1.

It is an object of this invention to provide a rapid colorimetric method for identifying the presence of residual ionic surfactants in aqueous solution and their concentration.

It is another object of this invention to provide a method suitable for field-testing water and waste water for either anionic or cationic surfactant-type pollutants. These objects, and others as will become apparent hereinafter, are accomplished by the present invention.

The colorimetric method of this invention is suitable for the analysis and detection of either anionic or cationic surfactants in aqueous solution. Advantages of the method of the present invention over standard methods such as the methylene blue method and the carbon adsorption method include its time-saving simplified procedures and its suitability for cationic surfactant analysis. Advantages of the method of the present invention over the method of my above-identified application are its greater speed and its greater accuracy for low residual concentrations of surfactants.

DESCRIPTION OF THE DRAWING

The FIGURE presents a simplified flow chart of the method of this invention.

According to this invention, and as shown in the FIGURE, the water sample is treated first with an excess amount of Azure A reagent and an appropriate buffer solution. In the presence of chloroform, the Azure A reacts with residual anionic surfactants and forms a chloroform-soluble, blue-colored complex. The intensity of the blue color in the vigorously rocked and subsequently settled chloroform layer is proportional to the concentration of the Azure A – anionic surfactant complex. The intensity of the Azure A – anionic surfactant complex can then be measured by making spectrophotometric readings of the chloroform solution at the optimum wavelength of the device used, e.g. the optimum wavelength for a Bausch & Lomb Spectronic 600 spectrophotometer is 623 nm. When the chloroform extractant is colorless, the water sample contains no residual anionic surfactant and a new sample is taken and tested for the presence of residual cationic surfactants. The new sample is treated first with an excess amount of methyl orange reagent and an appropriate buffer solution. In the presence of chloroform, the methyl orange will react with residual cationic surfactants and forms a chloroform-soluble, yellow-colored complex. The intensity of the yellow color in the vigorously rocked and subsequently settled chloroform layer is proportional to the concentration of the methyl orange-cationic surfactant complex. The intensity of the methyl orange-cationic surfactant complex can then be measured by making spectrophotometric readings of the chloroform solution at the optimum wavelength of the device used, e.g. 415 nm for a Bausch & Lomb Spectronic 600 spectrophotometer.

REAGENTS

1. Stock linear alkylate sulfonate (LAS) solution: weigh an amount of the reference material equal to 1.000 g LAS on a 100% active basis, dissolve in distilled water and dilute to one liter to obtain a concentration of 1.00 ml = 1.00 mg LAS. This solution should be stored in a refrigerator to minimize biodegradation.

2. Standard linear alkylate sulfonate (LAS) solution: dilute 50.00 ml of stock LAS solution to one liter with distilled water to obtain a concentration of 1.00 ml = 50.00 $\mu$ g LAS.

3. Azure A reagent: dissolve 400 mg of Azure A, and 5 ml of 1.0 N sulfuric acid in 500 ml of distilled water, and then make up to 1000 ml with distilled water.

4. Stock cetyldimechylbenzylammonium chloride (CDBAC) solution: Weigh an amount of the reference material equal to 1.000 g CDBAC on a 100% active basis. Dissolve in distilled water and dilute to one liter to obtain a concentration of 1.00 ml = 1.00 mg CDBAC.

5. Standard cetyldimethylbenzylammonium chloride (CDBAC) solution: Dilute 50.00 ml of stock CDBAC solution to one liter with distilled water; 1.00 ml = 50.0 $\mu$ g CDBAC.

6. Methyl-orange solution: dissolve 0.10 g methyl-orange powder in a small amount of distilled water. Dilute this volume to 100 ml, so that the concentration is 0.1% by weight.

7. Buffer solution: mix 250 ml of 0.5 M citric acid and 250 ml of 0.2 M disodium hydrogen orthophosphate together.

8. Chloroform, anhydrous.

IDENTIFICATION OF SAMPLE'S IONIC CHARGE

Pipette an aliquot amount of the water sample into a separatory funnel and dilute to 50 ml with distilled water. Add 1 ml of Azure A reagent, 5 ml of buffer solution and 25 ml of chloroform to the separatory funnel. Stopper the separatory funnel and shake it vigorously for 30 seconds. Allow the sample to stand undisturbed for 5 minutes after shaking. The chloroform will separate from the water and settle as a lower layer. If the chloroform layer is blue in color, anionic surfactants are present in the water sample and the sample can be analyzed therefor. If the chloroform layer is colorless, the sample does not contain an anionic surfactant and should be discarded. A new sample should then be prepared and analyzed for cationic surfactants.

ANIONIC SURFACTANT ANALYSIS

Taking a sample in which the chloroform layer is blue in color:

1. Wedge a small plug of glass wool in the stem of a filtering funnel. Place the filtering funnel above a clean, dry test cell having a 1 cm (or longer) light path and filter the chloroform layer through the glass wool to remove the water therefrom and collect the treated chloroform in the cell.
2. Determine the absorbance (or equivalent) of the chloroform solution in a spectrophotometer (or photometer) at a wavelength of 623 nm against a blank chloroform sample.
3. Refer to a previously prepared calibration curve of absorbance v. concentration of LAS (in mg/l) for anionic surfactants and determine the equivalent LAS content (in mg/l) from the calibration curve.

CATIONIC SURFACTANT ANALYSIS

Taking a new sample if the original sample was colorless when Azure A reagent, buffer solution and chloroform were added:

1. Pipette an aliquot amount of the water sample into a separatory funnel, dilute to 50 ml with distilled water.
2. Add 1 ml of methyl orange reagent, 5 ml of buffer solution, and 50 ml of chloroform to the separatory funnel. Stopper the separatory funnel and shake it vigorously for 30 seconds. Allow the sample to stand, undisturbed for 20 minutes after shaking. The chloroform will separate from the water and settle as a lower layer.
3. Wedge a small plug of glass wool in the stem of a filtering funnel. Place the filtering funnel above a clean, dry test cell (10 cm light path) and filter the chloroform layer through the glass wool to remove the water therefrom. Collect the treated chloroform in the cell.
4. Determine the absorbance (or equivalent) of the chloroform solution in a spectrophotometer (or photometer) at a wavelength of 415 nm against a blank chloroform sample.
5. Refer to a previously prepared calibration curve of absorbance v. concentration of CDBAC (in mg/1) for cationic surfactants and determine the equivalent CDBAC content (in mg 1) from the calibration curve of cationic surfactant.

MODIFICATIONS

Where a color disc, a color comparison chart, or a set of Nessler tubes are used in the field to replace a spectrophotometer or photometer, the color developed in the indicator-sample-chloroform solution will give the surfactant concentration when the treated chloroform is compared with a color comparison chart, a color disc, or a set of Nessler tubes.

Methylene blue can be used to replace the Azure A and cationic surfactants other than cetyldimethylbenzylammonium chloride can be used as the standard cationic surfactant. The optimum wavelength for other reagents will be different, 652 nm for methylene blue.

Although the preferred method of practicing the present invention has been described, other changes will occur to those skilled in the art. It is therefore intended that the scope of the present invention is to be limited only by the scope of the appended claims.

I claim:

1. A method for the analysis of residual anionic and cationic surfactants present in an aqueous solution including the steps of:
    obtaining a known volume first sample of the aqueous solution to be tested;
    adding buffer solution, a first dye reagent and chloroform to the first sample and mixing thoroughly to permit the formation of a water-chloroform two-phase mixture;
    allowing the first sample to stand undisturbed to permit the separation of chloroform from the two-phase mixture, the separated chloroform layer being colored in the presence of residual anionic surfactants in the first sample;
    if the separated chloroform layer is colored, colorimetrically determining the concentration of the residual anionic surfactants which are directly related to the intensity of the color of the chloroform layer; and
    if the chloroform layer of the two-phase mixture of the first sample is not colored the first sample contains no residual anionic surfactants and the following further steps are carried out:
    a. obtaining a known volume second sample of the aqueous solution to be tested;
    b. adding buffer solution, a second dye reagent and chloroform to the second sample and mixing thoroughly to permit the formation of a water-chloroform two-phase mixture;
    c. allowing the second sample to stand undisturbed to permit the separation of chloroform from the two-phase mixture, the separated chloroform layer of the second sample being colored in the presence of residual cationic surfactants in the second sample; and
    d. if the separated chloroform layer of the second sample is colored, colorimetrically determining the concentration of the residual cationic surfactants which are directly related to the intensity of the color of the chloroform layer of the second sample, if the chloroform layer of two-phase mixture of the second sample is not colored the second sample contains no residual ionic surfactants.

2. The method of claim 1 wherein said first dye reagent is Azure A.

3. The method of claim 2 wherein said second dye reagent is methyl orange.

4. The method of claim 1 wherein a spectrophotometer is used for colorimetrically determining the concentration of said residual anionic and cationic surfactants.

5. The method of claim 1 wherein a photometer is used for colorimetrically determining the concentration of said residual anionic and cationic surfactants.

6. The method of claim 1 wherein a color comparison chart is used for colorimetrically determining the concentration of said residual anionic and cationic surfactants.

7. The method of claim 1 wherein a color disc is used for colorimetrically determining the concentration of said residual anionic and cationic surfactants.

8. The method of claim 1 wherein a set of Nessler tubes is used for colorimetrically determining the concentration of said residual anionic and cationic surfactants.

* * * * *